(12) United States Patent
Fujii et al.

(10) Patent No.: US 7,870,777 B2
(45) Date of Patent: Jan. 18, 2011

(54) GAS SENSOR

(75) Inventors: Yoshiyasu Fujii, Nagoya (JP); Takayoshi Atsumi, Konan (JP); Hideya Inukai, Ogaki (JP); Naoki Yamada, Iwakura (JP); Takeo Mizui, Konan (JP)

(73) Assignee: NGK Spark Plug Co., Ltd., Aichi (JP)

( * ) Notice: Subject to any disclaimer, the term of this patent is extended or adjusted under 35 U.S.C. 154(b) by 456 days.

(21) Appl. No.: 12/107,342

(22) Filed: Apr. 22, 2008

(65) Prior Publication Data
US 2008/0257016 A1 Oct. 23, 2008

(30) Foreign Application Priority Data
Apr. 23, 2007 (JP) .............................. 2007-113100

(51) Int. Cl.
*G01N 9/00* (2006.01)
(52) U.S. Cl. ..................................... 73/31.05; 73/23.2
(58) Field of Classification Search ................ 73/31.05, 73/23.2
See application file for complete search history.

(56) References Cited

U.S. PATENT DOCUMENTS

| 6,758,952 | B2 | 7/2004 | Ishikawa |
| 7,036,352 | B2 * | 5/2006 | Isomura et al. .............. 73/23.2 |
| 2005/0029101 | A1 * | 2/2005 | Isomura et al. ............. 204/428 |

FOREIGN PATENT DOCUMENTS

JP 2006-208165 A 8/2006

* cited by examiner

*Primary Examiner*—Hezron Williams
*Assistant Examiner*—Rodney T Frank
(74) *Attorney, Agent, or Firm*—Sughrue Mion, PLLC (57) ABSTRACT

A gas sensor having an axis including a detecting element; a metal shell; an outer cylinder; and a plug member, as defined herein, and the gas sensor includes a first protective member that covers an air vent of the plug member so as to protect the filter member, the protective member having a ventilation portion having an opening smaller than an opening of the air vent and at least partially overlapping the air vent in the axial direction, and at least one of the outer cylinder and the plug member is provided with a locking portion that limits rotation of the protective member around the axis.

15 Claims, 9 Drawing Sheets

GAS SENSOR

BACKGROUND OF THE INVENTION

1. Field of the Invention

The present invention relates to a gas sensor having a ventilation structure for holding a detecting element that detects a gas to be detected inside a metal shell or an outer cylinder, and for securing air permeability between the inside and outside of the outer cylinder.

2. Description of the Related Art

Conventionally known is a gas sensor provided with a detecting element that detects a specific gas component (for example, oxygen, etc.) in exhaust gas discharged from an internal combustion engine, using a solid electrolyte made of ceramic, such as zirconia. For example, a detecting element of an oxygen sensor that detects oxygen has a configuration in which a detecting electrode exposed to exhaust gas and a reference electrode exposed to a reference gas (typically the atmosphere) are formed on a solid electrolyte as a pair so as to sandwich the electrolyte. The detecting element detects oxygen in the exhaust gas by an electromotive force generated between the subject electrodes according to a difference in oxygen partial pressure between the exhaust gas and the reference gas (atmosphere).

When such an oxygen sensor is attached to an exhaust pipe of an internal combustion engine, the detecting element is held in a metal shell in a state where it is exposed directly or indirectly to the outside so that the detecting electrode may be exposed to exhaust gas that flows through the exhaust pipe. Also, the detecting electrode and the reference electrode are separated by an outer casing fixed to the metal shell, and the metal shell. Further, a lead wire for extracting a detection signal of the detecting element is pulled outside of the outer casing, and a plug member for closing an outlet for the lead wire is attached to the outlet.

The plug member (grommet) is provided with an atmosphere communication hole (through hole) for securing air permeability between the inside and outside of the outer casing external to the exhaust pipe so as to introduce the atmosphere toward the reference electrode, in addition to lead wire insertion holes that allow lead wires (a sensor output lead wire and a heater lead wire) to be inserted therethrough. Also, the atmosphere communication hole of the plug member is provided with a filter member for introducing the atmosphere into the outer casing, but which prevents water droplets or the like from entering the outer casing (for example, refer to JP-A-2006-208165).

3. Problems to be Solved by the Invention

However, in the oxygen sensor of JP-A-2006-208165, the filter member is directly exposed to the outside environment. Typically, since the oxygen sensor is disposed near a road surface of an automobile, the filter member is susceptible to external impact, such as contact with plants and trees, or collision with scattering stones, and the filter member may become damaged. Also, if the filter member is damaged, and if the oxygen sensor becomes wet, there is a possibility that water may enter the oxygen sensor. This in turn causes an abnormality in the output of the oxygen sensor, or short-circuiting of a terminal.

SUMMARY OF THE INVENTION

The invention has been made in order to solve the above problems, and an object thereof is to provide a gas sensor capable of protecting a filter member provided in an atmosphere communication hole which serves to introduce the atmosphere (e.g., air) to the gas sensor (more specifically, to a reference electrode of the gas sensor).

In accordance with a first aspect of the invention, the above object has been achieved by providing a gas sensor having an axis comprising: a detecting element extending in an axial direction of the gas sensor, and having a detecting portion for detecting a gas to be detected on a leading end side of the detecting element; a metal shell surrounding a radial periphery of the detecting element such that the detecting portion protrudes from a leading end of the metal shell; an outer cylinder that is fixed to the metal shell, and which surrounds the radial periphery on the rear end side of the detecting element; and a plug member provided in a rear end side of the outer cylinder, the plug member including a lead wire insertion hole through which a lead wire is inserted, and an air vent provided with a filter member having air permeability and waterproofness. The gas sensor comprises a first protective member that covers the air vent of the plug member so as to protect the filter member, the first protective member having a ventilation portion having an opening smaller than an opening of the air vent and at least partially overlapping the air vent in the axial direction. Also, a least one of the outer cylinder and the plug member is provided with a locking portion that regulates or rather limits rotation of the first protective member (in a peripheral direction) around the axis.

Further, in a second aspect of the invention, in addition to the configuration described in the first aspect, the first protective member is mechanically joined to the outer cylinder so that the first protective member is spaced away from the lead wire.

Further, in a third aspect of the invention, in addition to the configuration described in the first or second aspect, the distance between the first protective member and the lead wire is 1 mm or more.

Further, in a fourth aspect of the invention, in addition to the configuration described in any one of the first to third aspects, the first protective member comprises a plurality of arm portions that extend radially outward from the ventilation portion and a cylindrical latch portion that is connected to individual ones of the plurality of the arm portions, said cylindrical latch portion surrounding the radial periphery on the rear end side of the outer cylinder and being mechanically joined to the outer cylinder, the locking portion comprises a groove which extends radially outward from the air vent on a rear end surface of the plug member so as to avoid the lead wire insertion hole, and at least one of the arm portions is provided in the groove.

Further, in a fifth aspect of the invention, in addition to the configuration described in the fourth aspect, the latch portion that has a cylindrical shape comprises a plurality of inwardly protruding portions engaged with a crimping portion formed in an outer peripheral surface of the outer cylinder.

Further, in a sixth aspect of the invention, in addition to the configuration described in the fourth or fifth aspects, the groove is a connecting groove that symmetrically extends radially outward from the air vent on the rear end surface of the plug member, and two of the plurality of arm portions are provided in the connecting groove.

Further, in a seventh aspect of the invention, in addition to the configuration described in any one of the first to sixth aspects, the ventilation portion of the first protective member comprises at least one of (i) a plurality of holes penetrating therethrough; and (ii) a mesh member assembled to an axial opening provided in the ventilation portion of the first protective member.

Further, in an eighth aspect of the invention, in addition to the configuration described in any one of the first to seventh aspects, the first protective member has a hardness greater than that of the filter member.

Further, the gas sensor according to a ninth aspect of the invention is a gas sensor having an axis comprising: a detecting element extending in an axial direction of the gas sensor, and having a detecting portion for detecting a gas to be detected on a leading end side of the detecting element; a metal shell surrounding a radial periphery of the detecting element such that the detecting portion protrudes from a leading end of the metal shell; an outer cylinder that is fixed to the metal shell, and which surrounds the radial periphery on a rear end side of the detecting element; and a plug member provided in a rear end of the outer cylinder, the plug member including a lead wire insertion hole through which a lead wire is inserted, and an air vent provided with a filter member having air permeability and waterproofness. The gas sensor comprises a second protective member that has a covering portion that covers the filter member so that the filter member cannot be viewed in the axial direction from the rear side, the second protective member being mechanically joined to the outer cylinder so as to form a gap between the second protective member and the plug member, and at least one of the outer cylinder and the plug member is provided with a locking portion that limits rotation of the second protective member (in a peripheral direction) around the axis.

Further, in a tenth aspect of the invention, in addition to the configuration described in the ninth aspect, the first protective member is mechanically joined to the outer cylinder so that the second protective member is spaced away from the lead wire.

Further, in an eleventh aspect of the invention, in addition to the configuration described in the ninth or tenth aspects, the distance between the second protective member and the lead wire is 1 mm or more.

Further, in a twelfth aspect of the invention, in addition to the configuration described in any one of the ninth to eleventh aspects, the second protective member comprises a plurality of arm portions that extend radially outward from the covering portion and a cylindrical latch portion surrounding that is connected to individual ones of the plurality of the arm portions, said cylindrical latch portion the radial periphery on the rear end of the outer cylinder, and being mechanically joined to the outer cylinder, the locking portion comprises a groove which extends radially outward from the air vent on a rear end surface of the plug member so as to avoid the lead wire insertion hole, and at least one of the arm portions is provided in the groove.

Further, in a thirteenth aspect of the invention, in addition to the configuration described in the twelfth aspect, the latch portion that has a cylindrical shape comprises a plurality of inwardly protruding portions engaged with a crimping portion formed in an outer peripheral surface of the outer cylinder.

Further, in a fourteenth aspect of the invention, in addition to the configuration described in the twelfth or thirteenth aspect, the groove is a connecting groove that symmetrically extends radially outward from the air vent on the rear end surface of the plug member, and two of the plurality of arm portions are provided in the connecting groove.

Further, in a fifteenth aspect of the invention, in addition to the configuration described in any one of the ninth to fourteenth aspects, the second protective member has a hardness greater than that of the filter member.

In the gas sensor of the invention according to the first aspect, a first protective member is provided outside of the outer cylinder that protects the filter member and covers the air vent (atmosphere communication hole) of the plug member. Thus, the filter member will not be directly exposed to the outside via the air vent. Therefore, the filter member is not subject to direct external impact to thereby prevent damage to the filter member. As a result, water can be prevented from entering into the gas sensor. On the other hand, the ventilation portion is provided at least in the region of the first protective member that overlaps the air vent of the plug member in the axial direction. However, the ventilation portion has an opening smaller than the opening of the air vent. Thus, air permeability can be secured between the inside and outside of the outer cylinder via the air vent in a state where the filter member is not directly exposed to the outside via the air vent. Also, since the first protective member is assembled to the outer cylinder by mechanical joining, labor, such as crimping or welding, is unnecessary, and assembly of the gas sensor is simplified.

Meanwhile, the first protective member is assembled so as to surround a rear end side of the outer cylinder and so as to cover the air vent of the plug member. However, the lead wire insertion hole for a lead wire along with the air vent is formed in the plug member so as to extend in the axial direction. That is, a lead wire is also inserted through the lead wire insertion hole so as to extend along the axial direction. Consequently, when the first protective member is mechanically joined to the outer cylinder, it may rotate around the axis of the gas sensor after joining, to thereby damage the lead wire. Thus, in the gas sensor according to the invention, by providing a locking portion in at least one of the outer cylinder and the plug member, the first protective member assembled to the outer cylinder can be restrained from rotating around the axis. For this reason, the first protective member is spaced away from the lead wire. Thus, the possibility of damage or the like to the lead wire can be reduced.

Of course, because the locking portion limits rotation of the first protective member around the axis, the lead wire is not cut even in a state where the first protective member contacts the lead wire. However, in a case where the gas sensor receives, for example, a load caused by vibration from the outside, there is a possibility that wear or the like caused by contact friction may occur in a state where the first protective member and the lead wire abut one another. Thus, in the invention according to the second aspect, preferably, the first protective member is mechanically joined to the outer cylinder so that the first protective member is spaced away from the lead wire. In this case, in the invention according to the third aspect, the distance between the first protective member and the lead wire is preferably 1 mm or more.

If a crimping portion formed to fix the plug member to the outer cylinder is utilized and the first protective member is mechanically joined to the crimping portion by external fitting when the first protective member is mechanically joined to the outer cylinder, assembly can be easily performed without newly forming a portion for attaching the first protective member to the outer cylinder or the plug member.

Meanwhile, so as not to deteriorate the ventilation performance of the air vent when the plug member gets wet from the outside, the plug member may be provided with a groove for supporting drainage. In the invention according to the fourth aspect, if the groove is utilized as the locking portion, and the first protective member having arm portions that extend radially outward from the ventilation portion is used so as to engage the groove, a portion for engaging the locking portion need not be newly formed in the first protective member.

Moreover, by forming the latch portion in a cylindrical shape to cover the rear end of the outer cylinder, thereby establishing mechanical joining, after the first protective member is mechanically joined to the outer cylinder, the mechanical strength of the latch portion can be increased, wobbling of the latch portion with respect to the rear end of the outer cylinder can be suppressed, wobbling of the ventilation portion connected to the latch portion via the arm portions can be suppressed, and the filter member can be reliably protected.

Moreover, in the invention according to the fifth aspect, if the inwardly protruding portions are fashioned to protrude inwardly from the inner peripheral surface of the cylindrical latch portion, and the inwardly protruding portions engage a crimping portion of the outer cylinder, mechanical joining to the crimping portion can be maintained by the protruding portions, and wobbling of the first protective member can be suppressed. Also, since a clearance can be provided between the inner peripheral surface of the latch portion and the outer peripheral surface of the outer cylinder, it is easy to cover the latch portion on the rear end side of the outer cylinder when the first protective member is attached at the time of assembly. Such inwardly protruding portions may be formed by joining a projection to the inner peripheral surface of the latch portion, by forming the outer peripheral surface of the latch portion in the shape of a dowel that is pushed inward, or by making a slit and pushing its free end side inward. In this case, the inwardly protruding portions can have a spring property, and can more reliably suppress wobbling of the latch portion with respect to the outer cylinder while engaging the crimping portion with a biasing force.

Also, the above groove may be a connecting groove that symmetrically extends radially outward from the air vent for drainage. In this case, in the invention according to the sixth aspect, preferably two of the arm portions are provided in the connecting groove. By providing the arm portions in the connecting groove (that is, two arm portions are arranged symmetrically with respect to one another), the first protective member can be stably fixed to the plug member.

In addition, the ventilation portion of the first protective member desirably has a structure capable of covering and protecting the filter member from the outside, and sufficiently maintaining air permeability between the inside and outside of the outer cylinder. Thus, in the invention according to the seventh aspect, the ventilation portion is provided with at least one hole penetrating therethrough. Also, a mesh-like member may be assembled to an opening provided in the axial direction. If the ventilation portion is formed in any one form of such forms, the filter member can be protected, and air permeability can be secured.

In this case, in the invention according to the eighth aspect, the first protective member preferably has a hardness greater than that of the filter member. This can more reliably prevent the filter member from damage.

In the gas sensor of the invention according to the ninth aspect, the second protective member has a covering portion that covers the filter member so that the filter member cannot be viewed in the axial direction from the rear side. Thus, the filter member will not be directly exposed to the outside via the air vent. The filter member is not subject to direct external impact, to thereby protect the filter member from damage. As a result, entry of water into the gas sensor can be prevented. Meanwhile, the second protective member has a configuration that allows ventilation between the inside of the air vent and the outside via a gap between the second protective member and the plug member. As a result, air permeability between the inside and outside of the outer cylinder can be secured via the air vent in a state where the filter member is not directly exposed to the outside via the air vent. Also, since the second protective member is assembled to the outer cylinder by mechanical joining, labor, such as crimping or welding, is unnecessary, and assembly of the gas sensor is simplified.

Meanwhile, the second protective member is assembled so as to surround the rear end of the outer cylinder and cover the air vent of the plug member. However, the lead wire insertion hole for a lead wire along with the air vent is formed in the plug member so as to extend in the axial direction. That is, a lead wire is also inserted through the lead wire insertion hole so as to extend along the axial direction. Consequently, when the second protective member is mechanically joined to the outer cylinder, it may rotate around the axis of the gas sensor after joining, to thereby damage the lead wire. Thus, in the gas sensor according to the invention, by providing a locking portion in at least one of the outer cylinder and the plug member, the second protective member assembled to the outer cylinder can be restrained from rotating around the axis. For this reason, the second protective member is spaced away from the lead wire. Thus, the possibility of damage or the like to the lead wire can be reduced.

Of course, since the arm portions of the second protective member are provided in the groove, and thereby, the second protective member does not rotate around the axis, the lead wire is not cut even in a state where the second protective member contacts the lead wire. However, in a case where the gas sensor receives, for example, a load caused by vibration from the outside, there is a possibility that wear or the like caused by contact friction may occur in a state where the second protective member and the lead wire abut one another. Thus, in the invention according to a tenth aspect, preferably, the second protective member is mechanically joined to the outer cylinder so that the second protective member is spaced away from the lead wire. In this case, in the invention according to the eleventh aspect, the distance between the second protective member and the lead wire is preferably 1 mm or more.

If a crimping portion formed to fix the plug member to the outer cylinder is utilized and the second protective member is mechanically joined to the crimping portion by external fitting when the second protective member is mechanically joined to the outer cylinder, assembly can be easily performed without newly forming a portion for attaching the second protective member to the outer cylinder or the plug member.

Meanwhile, so as not to deteriorate the ventilation performance of the air vent when the plug member gets wet from the outside, the plug member may be provided with a groove for supporting drainage. In the invention according to the twelfth aspect, if the groove is utilized as the locking portion, and the second protective member having arm portions that extend radially outward from the ventilation portion is used so as to engage the groove, a portion for engaging the locking portion need not be newly formed in the second protective member.

Moreover, by forming the latch portion in a cylindrical shape to cover the rear end of the outer cylinder, thereby establishing mechanical joining, after the second protective member is mechanically joined to the outer cylinder, the mechanical strength of the latch portion can be increased, wobbling of the latch portion with respect to the rear end of the outer cylinder can be suppressed, wobbling of the covering portion connected to the latch portion via the arm portions can be suppressed, and the filter member can be reliably protected.

Moreover, in the invention according to the thirteenth aspect, if the inwardly protruding portions are fashioned to protrude inwardly from the inner peripheral surface of the cylindrical latch portion, and the inwardly protruding portions engage a crimping portion of the outer cylinder, mechanical joining to the crimping portion can be maintained by the protruding portions, and wobbling of the second protective member can be suppressed. Also, since a clearance can be provided between the inner peripheral surface of the latch portion and the outer peripheral surface of the outer cylinder, it is easy to cover the latch portion on the rear end side of the outer casing when the second protective member is attached at the time of assembly. Such inwardly protruding portions may be formed by joining a projection to the inner peripheral surface of the latch portion, by forming the outer peripheral surface of the latch portion in the shape of a dowel that is pushed inward, or by making a slit and pushing its free end side inward. In this case, the inwardly protruding portions can have a spring property, and can more reliably suppress wobbling of the latch portion with respect to the outer cylinder while engaging the crimping portion with a biasing force.

Also, the above groove may be a connecting groove that symmetrically extends radially outward from the air vent for drainage. In this case, in the invention according to the fourteenth aspect, preferably two of the arm portions are provided in the connecting groove. By providing the arm portions in the connecting groove (that is, two arm portions are arranged symmetrically with respect to one another), the second protective member can be stably fixed to the plug member.

In this case, in the invention according to the fifteenth aspect, preferably, the second protective member has a hardness that is greater than that of the filter member. This can further protect the filter member from damage.

DESCRIPTION OF REFERENCE NUMERALS

Reference numerals used to identify various structural features in the drawings include the following.
1: gas sensor
3: outer cylinder
5: metal shell
6: detecting element
9: grommet
18: lead wire
35: crimping portion
64: detecting portion
87: filter member
91: air vent
92: lead wire insertion hole
93, 94, 95, 96: groove
100: protective member
110: ventilation portion
116: opening
120, 125, 130, 135: arm portion
150: latch portion
155: inwardly protruding portion
200: gas sensor
205: protective member
210: covering portion
220, 230: arm portion
250: latch portion
255: inwardly protruding portion

DETAILED DESCRIPTION OF THE INVENTION

Hereinafter, an embodiment of a gas sensor of the invention will be explained with reference to the drawings. However, the present invention should not be construed as being limited thereto.

Figure 1:
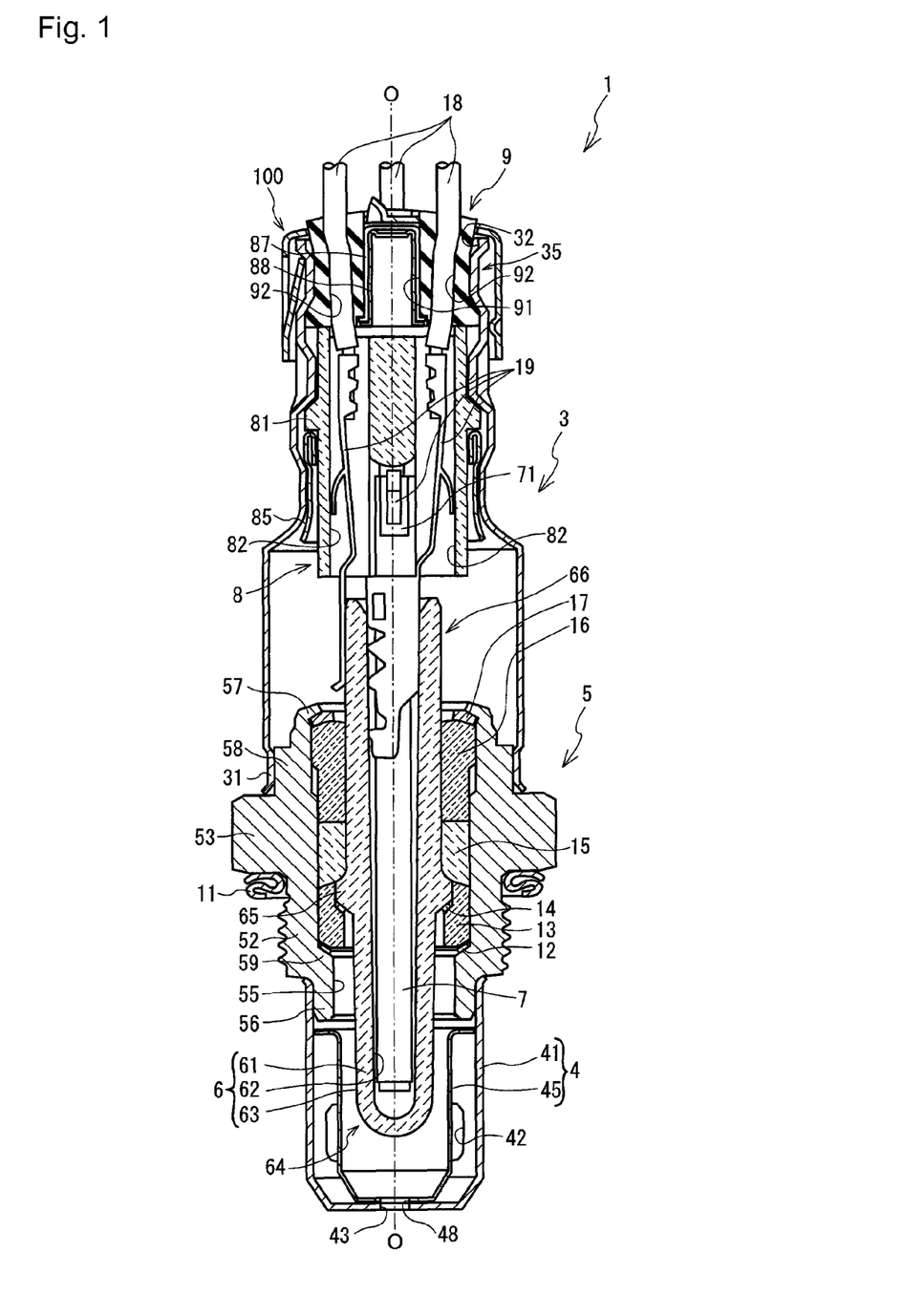
FIG. 1 is a longitudinal sectional view showing the structure of a gas sensor 1 of a first embodiment.
Figure 2:
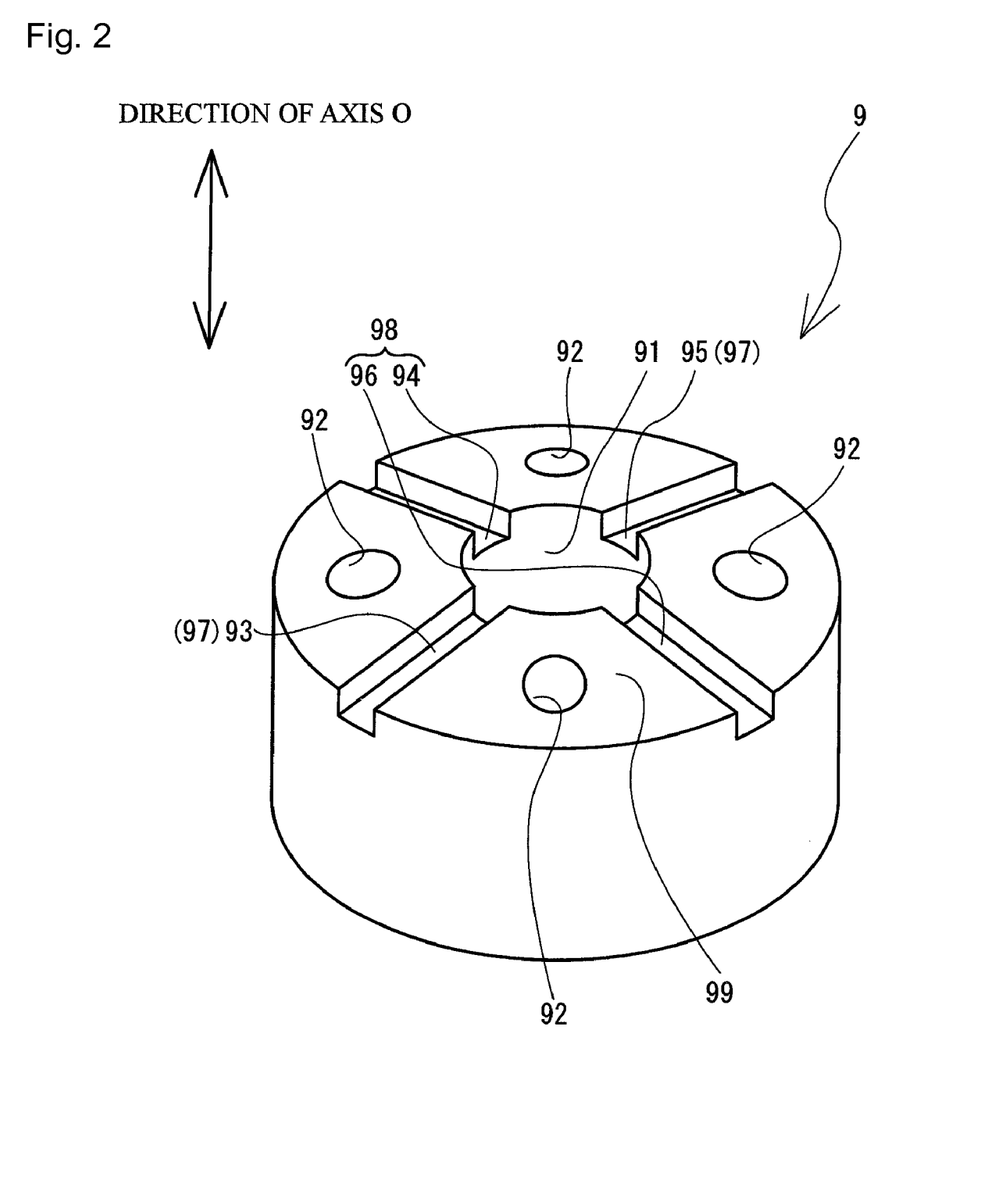
FIG. 2 is a perspective view of a grommet 9.
Figure 3:
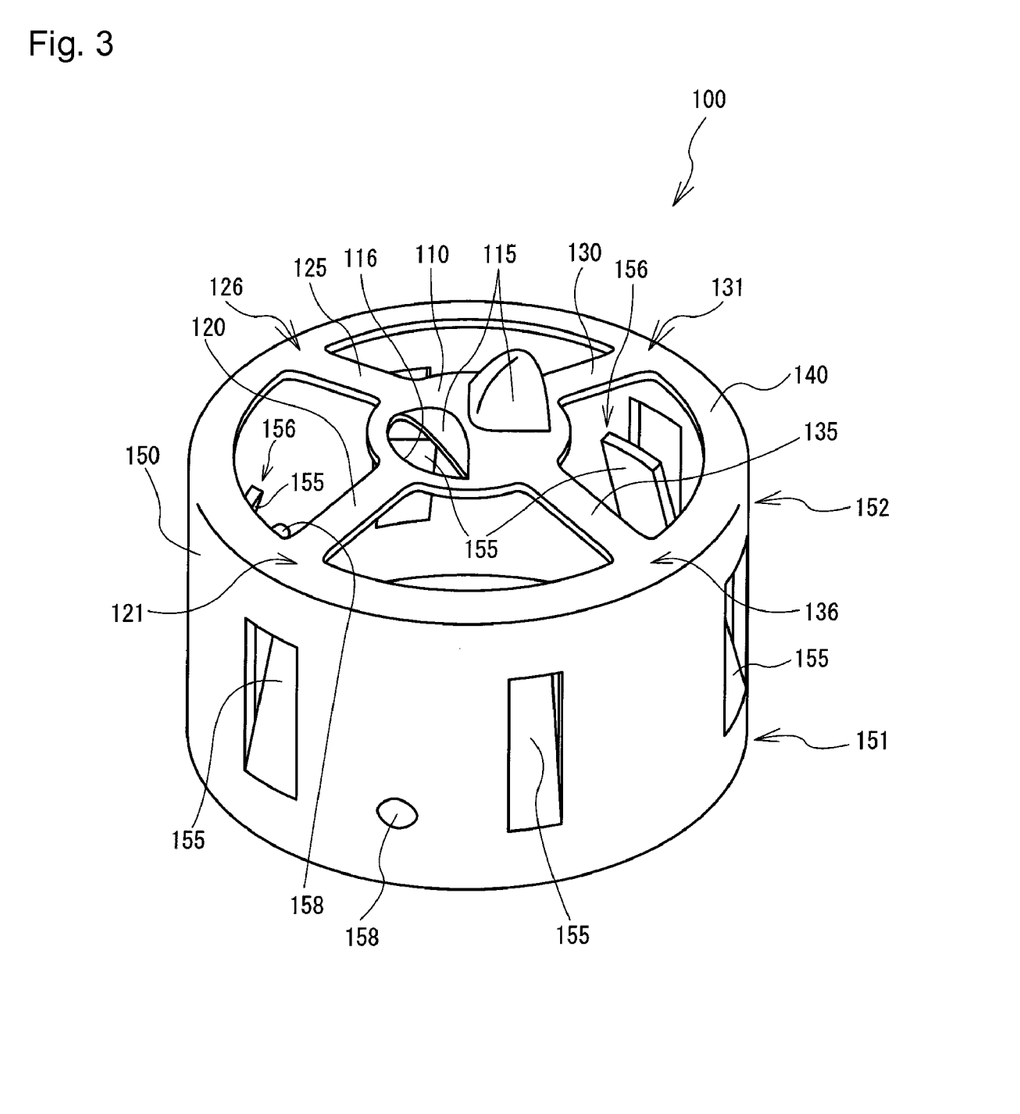
FIG. 3 is a perspective view of a protective member 100 of the first embodiment.
Figure 4:
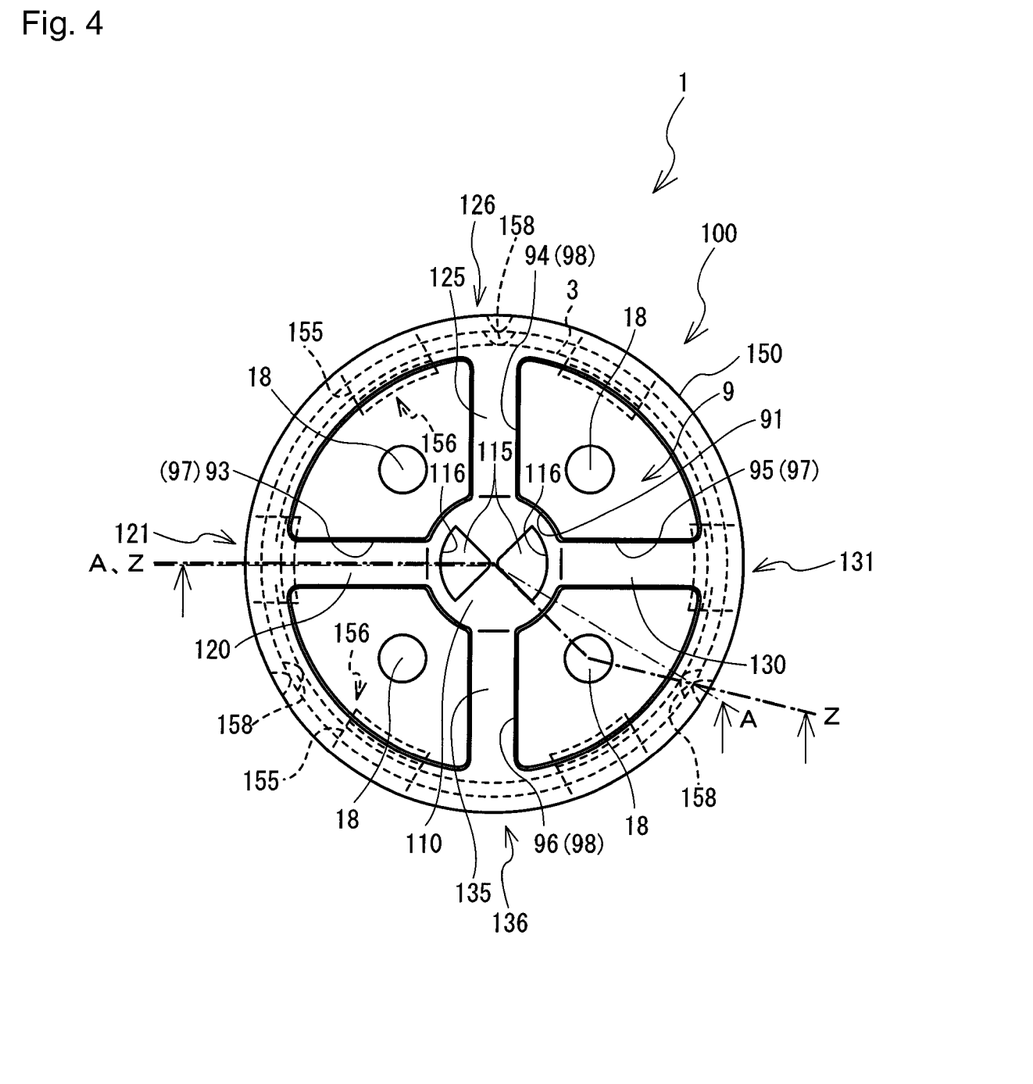
FIG. 4 is a view of the gas sensor 1 when seen from the rear end side in the direction of an axis O (the upper side in FIG. 1).
Figure 5:
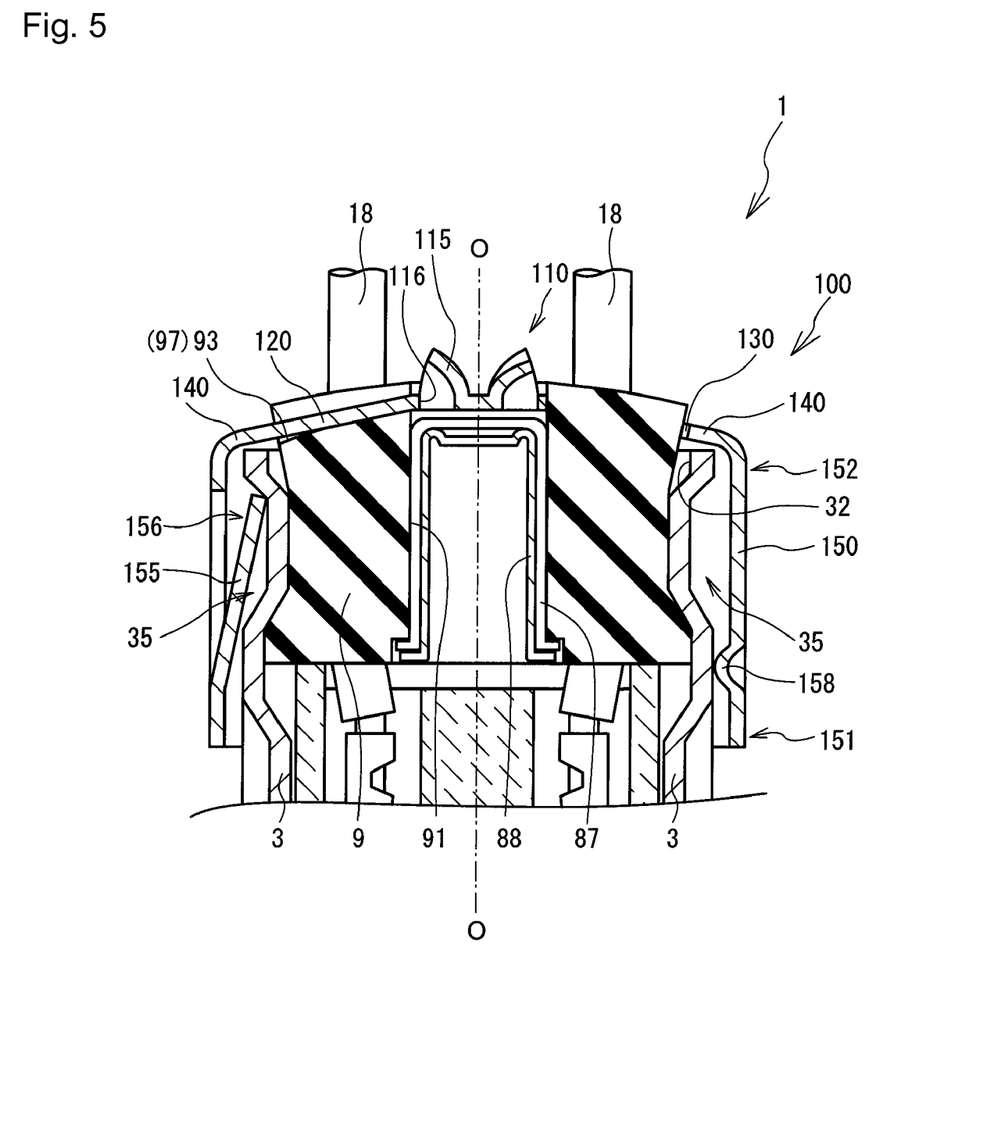
FIG. 5 is a partially enlarged sectional view of the rear end side of the gas sensor 1 when seen from the direction of an arrow in a bent line A-A shown by a one-dot chain line of FIG. 4.

First, the structure of a gas sensor 1 of a first embodiment will be explained as an example with reference to FIGS. 1 to 5. FIG. 1 is a longitudinal sectional view showing the structure of the gas sensor 1 of the first embodiment. FIG. 2 is a perspective view of a grommet 9. FIG. 3 is a perspective view of a protective member 100 of the first embodiment. FIG. 4 is a view of the gas sensor 1 when seen from the rear end side in the direction of an axis O (the upper side in FIG. 1). FIG. 5 is a partially enlarged sectional view of the rear end side of the gas sensor 1 when seen from the direction of an arrow in a bent line A-A shown by a one-dot chain line of FIG. 4.

In addition, the gas sensor 1 shown in FIG. 1 is used while being attached to an exhaust pipe (not shown) for exhaust gas exhausted from an internal combustion engine of an automobile or the like. In the following description, the side (closed side and lower side in the drawing) that faces a leading end of a detecting element 6, which is inserted into the exhaust pipe, in the direction of an axis O is the leading end side, and the side (upper side in the drawing) that faces the side opposite the leading end side is the rear end side.

The gas sensor 1 shown in FIG. 1 is a sensor for detecting the presence/absence of oxygen in exhaust gas that flows through an exhaust pipe, and has a structure in which an elongate cylindrical detecting element 6 whose tip is closed is held in a metal shell 5, an outer cylinder 3, and a protector 4. A lead wire 18 for extracting a signal that is output by the detecting element 6 or for applying an electric current to a heater 7 juxtaposed to the detecting element 6 is pulled out of the gas sensor 1, or is electrically connected to a sensor control unit located away from the gas sensor 1, or to an electronic control unit (ECU) of an automobile, which is not shown.

In the detecting element 6 of the gas sensor 1, a solid electrolyte 61 made of zirconia as its major component and that is formed in the shape of a bottomed tube that extends in the direction of an axis O constitutes a base. A porous reference electrode 62 made of Pt or a Pt alloy is formed on the inner surface of the solid electrolyte 61 so as to cover almost the entire surface thereof. A porous detecting electrode 63 made of Pt or a Pt alloy is formed so as to cover almost the entire outer surface of the solid electrolyte 61, similarly to the reference electrode 62. The tip (closed side) of the detecting element 6 constitutes a detecting portion 64, and the external detecting electrode 63 is exposed to exhaust gas that flows through the exhaust pipe (not shown). Although not shown, the detecting electrode 63 is covered with a porous electrode protection layer made of a heat-resistant ceramic, and is protected from poisoning by the exhaust gas. Further, a collar-like flange portion 65 that protrudes radially outward is provided almost in an intermediate position of the detecting element 6 in the direction of the axis O. Also, a rod-like heater 7 for heating the solid electrolyte 61 to activate the same is inserted into the tube of the detecting element 6.

The detecting element 6 is held in a cylindrical hole 55 of the metal shell 5 in a state where the radial periphery thereof is surrounded by the cylindrical metal shell 5. The metal shell 5 is a cylindrical member made of stainless steel, such as SUS430, and an externally threaded portion 52 screwed to an attachment portion (not shown) of the exhaust pipe is formed on the leading end side of the metal shell. A leading end engaging portion 56 engaged with the protector 4 to be described below is formed at an outer periphery of the metal shell closer to the leading end side than the external threaded portion 52. The detecting portion 64 of the detecting element 6 is made to protrude more toward the leading end side than the leading end engaging portion 56.

A tool engaging portion 53 whose diameter is enlarged in the radial direction is formed on the rear end side of the externally threaded portion 52 of the metal shell 5, for engaging an attachment tool for attaching the gas sensor 1 to the attachment portion (not shown) of the exhaust pipe. An annular gasket 11 for preventing leakage of gas via the attachment portion of the exhaust pipe is inserted into a portion between the tool engaging portion 53 and the externally threaded portion 52. Also, a crimping portion 57 for crimping and fixing the detecting element 6 held within the cylindrical hole 55 is provided on the rear end side of the metal shell 5. A rear end 66 of the detecting element 6 is made to protrude more toward the rear end side than the crimping portion 57. A rear end engaging portion 58 that engages a leading end 31 of the outer cylinder 3 to be described below is formed at an outer periphery of the metal shell between the tool engaging portion 53 and the crimping portion 57.

Next, a stepped portion 59 that is formed by making an inner periphery of the metal shell protrude radially inward is provided on the leading end side of the cylindrical hole 55 of the metal shell 5, and a cylindrical supporting member 13 made of alumina is locked to the stepped portion 59 via metallic packing 12. An inner periphery of the supporting member 13 is also formed in a stepped shape, and the flange portion 65 of the detecting element 6 is supported by the supporting member 13 via a metallic packing 14 disposed in the stepped portion. Furthermore, a filling member 15 made of talc powder is filled into the cylindrical hole 55 on the rear end side of the supporting member 13, and a cylindrical sleeve 16 made of alumina is disposed on the rear end side of the filling member 15 so as to sandwich the filling member 15 between the cylindrical sleeve and the supporting member 13.

An annular ring 17 is disposed on the rear end side of the sleeve 16, and the sleeve 16 is pressed against the filling member 15 via the ring 17 by crimping the crimping portion 57 of the metal shell 5 in the direction of an inner leading end. Through crimping of crimping portion 57, the filling member 15 is compressed and filled so as to press the flange portion 65 of the detecting element 6 toward the supporting member 13 locked to the stepped portion 59 of the metal shell 5, and a gap between an inner peripheral surface of the cylindrical hole 55 of the metal shell 5 and an outer peripheral surface of the detecting element 6 are buried in an airtight manner. As such, the detecting element 6 is held within the cylindrical hole 55 of the metal shell 5 via each member sandwiched between the crimping portion 57 of the metal shell 5, and the stepped portion 59.

Next, the protector 4 that covers the detecting portion 64 of the detecting element 6 that is made to protrude toward the leading end side in the direction of the axis O from the leading end engaging portion 56 is welded to the leading end engaging portion 56 of the metal shell 5. The protector 4 protects the detecting portion 64 of the detecting element 6 that protrudes into the exhaust pipe when the gas sensor 1 is attached to the exhaust pipe (not shown), from collision of water drops, foreign matter, etc., present in the exhaust gas. The protector 4 is configured so as to form a double structure composed of a bottomed cylindrical outside protector 41, a peripheral edge on the open side of which is joined to the leading end engaging portion 56, and a bottomed cylindrical inside protector 45 that is fixed to the inside of the outside protector 41. Inlets 42 for introducing the exhaust gas inward, and guiding it to the detecting portion 64 of the detecting element 6 are respectively formed in outer peripheral surfaces of the outside protector 41 and the inside protector 45 (gas inlet of the inside protector 45 is not shown). Further, outlets 43 and 48 for discharging water drops or exhaust gas that has entered the inside are respectively formed in bottom surfaces of the outside protector 41 and the inside protector 45.

As described above, the rear end 66 of the detecting element 6 is made to protrude further rearward than the rear end (crimping portion 57) of the metal shell 5. A cylindrical separator 8 made of insulating ceramic is disposed closer to the rear end side in the direction of the axis O than the rear end 66. The separator 8 separates four connecting terminals 19 (three of the connecting terminals 19 are shown in FIG. 1) that are electrically connected to the reference electrode 62 and the detecting electrode 63 of the detecting element 6, and a pair of electrodes 71 (one electrode 71 of which is shown in FIG. 1) exposed on the rear end side for applying an electric current to a heating resistor of the heater 7 so that the connecting terminals do not contact one another, and has accommodation portions 82 into which the respective connecting terminals 19 are separately accommodated. The accommodation portions 82 pass through the separator 8 in the direction of the axis O, and are configured such that atmospheric communication between the leading end side and the rear end side of the separator 8 is allowed. Cores of four lead wires 18 are crimped and joined to the connecting terminals 19, respectively (three of the lead wires 18 are shown in FIG. 1), and the respective lead wires 18 are pulled outside the gas sensor 1 via the grommet 9 described below. Further, the flange portion 81 that protrudes radially outward is provided on an outer peripheral surface of the separator 8, and a substantially cylindrical holding fitting 85 is fitted into the outer peripheral surface of the separator closer to the leading end side than the flange portion 81.

Next, the rear end engaging portion 58 of the metal shell 5 is engaged with the leading end 31 of the cylindrical outer cylinder 3 made of stainless steel, such as SUS304. The leading end 31 is crimped from the outer peripheral side, and the leading end is subjected to laser welding around the outer periphery thereof, and is joined to the rear end engaging portion 58. The outer cylinder 3 extends toward the rear end side in the direction of the axis O, and radially surrounds the rear end 66 of the detecting element 6, or the outer periphery of the separator 8 disposed closer to the rear end side than the rear end. The outer peripheral surface of the outer cylinder 3 corresponding to an arrangement position of the separator 8 is crimped in the radial direction, and thereby, the holding fitting 85 holds the separator 8 therein, and is crimped and held inside the outer cylinder 3.

Further, a grommet 9 made of fluorine-based rubber is fitted into the opening 32 on the rear end side of the outer cylinder 3. As shown in FIG. 2, the grommet 9 is a plug member formed in a substantially cylindrical shape that has the direction of the axis O as its height direction, and closes the rear end side of the outer cylinder 3. A ceiling surface 99 that becomes the surface that faces the rear end at the time of attachment to the gas sensor 1 is formed as an inclined surface that rises toward the central side from the outer peripheral side in the radial direction. Also, the air vent 91 that passes through the ceiling surface in the direction of the axis O is formed in the radial center of the ceiling surface, and four lead wire insertion holes 92 that pass through the ceiling surface in the direction of the axis O are also formed in positions that are spaced at regular intervals in the peripheral direction, even closer to the outer peripheral side of the ceiling surface than the air vent 91. In addition, the grommet 9 corresponds to the "plug member" of the invention.

Here, as shown in FIG. 1, the air vent 91 is provided to introduce the atmosphere into the outer cylinder 3 that is closed by the grommet 9. Although the detecting element 6 is held by the metal shell 5 in a state where the rear end 66 protrudes into the outer cylinder 3, the reference electrode 62 formed in the tube of the detecting element 6 is configured so as to be exposed to the atmosphere via the air vent 91, and the accommodation portions 82 of the separator 8. Further, the four lead wires 18 that electrically connect the detecting electrode 63 and the reference electrode 62 of the detecting element 6, and that electrically connect the pair of electrodes 71 of the heater 7 with the sensor control unit or ECU (not shown), are independently inserted into the four lead wire insertion holes 92, respectively (a state where two of the lead wires 18 are inserted through the lead wire insertion holes 92 is shown in FIG. 1).

Further, as shown in FIG. 2, the four grooves 93, 94, 95 and 96 that extend in the radial direction from the air vent 91 toward the outer peripheral side are formed in the ceiling surface 99 of the grommet 9. The respective grooves 93 to 96 are arranged between two adjoining lead wire insertion holes 92, respectively, so as to avoid the four lead wire insertion holes 92 opening to the ceiling surface 99. The grooves 93 and 95 make a pair and constitute a connecting groove 97, the grooves 93 and 95 extending symmetrically with respect to the air vent 91 as an origin. Similarly, the grooves 94 and 96 also make a pair and constitute a connecting groove 98, the grooves 96 and 98 extending symmetrically with respect to the air vent 91 as an origin. Also, when the ceiling surface 99 is seen in the direction of the axis O, the connecting groove 97 and the connecting groove 98 are arranged so as to be orthogonal to each other and intersecting at the air vent 91.

As shown in FIG. 1, a filter member 87 and its anchoring fitting 88 are inserted into the air vent 91 of the grommet 9. The filter member 87 is a film type filter that has a micron-sized network structure formed from, for example, a fluororesin, such as PTFE (polytetrafluoroethylene), and is configured so as not to allow passage of water drops, etc., and so as to allow gas communication. The anchoring fitting 88, a member formed in a cylindrical shape, sandwiches the filter member 87 between its own outer periphery, and an inner periphery of the air vent 91, and fixes it to the grommet 9. The aforementioned grooves 93 to 96 of the grommet 9 form flow passages that lead the water drops, which cannot pass through the filter member 87, to the outer peripheral side so as not to accumulate on the filter member 87.

As such, the filter member 87 and the anchoring fitting 88 are inserted into the air vent 91, and the grommet 9 in which the lead wires 18 are inserted through the lead wire insertion holes 92 is fitted into the opening 32 of the outer casing 3 so as to abut the separator 8 from the rear end side. In this state, the portion of the outer cylinder 3 slightly closer to the leading end side than the opening 32 is crimped radially inward from the outer peripheral side, and the grommet 9 is fixed to the outer cylinder 3. In addition, the crimping portion 35 formed by crimping forms an annular groove that is depressed in the radial direction on the outer peripheral surface of the outer cylinder 3.

Next, a protective member 100 that covers the air vent 91 of the grommet 9, and protects the filter member 87 from outside impacts, such as contact with plants and trees, or collision with scattering stones, thereby preventing damage thereof, is attached to the rear end side of the outer cylinder 3. The protective member 100 is formed in the shape of a cap as shown in FIG. 3 by press-working a sheet material made of stainless steel, such as SUS. In addition, the protective member 100 corresponds to the "first protective member" of the invention.

The protective member 100 has a ventilation portion 110 that is obtained by shaping a metal plate into a circular plate. The ventilation portion 110 is formed with louvers 115 that are obtained by pushing and bending portions of the ventilation portion 110 so as to form openings 116. Four plate-like arm portions 120, 125, 130 and 135 that extend in four directions radially outward are formed at a peripheral edge of the ventilation portion 110. Leading ends 121, 126, 131 and 136 of the respective arm portions 120, 125, 130 and 135 in their extension directions are inclined toward the bottom surface side (downward) of the ventilation portion 110 in its thickness direction. When the protective member 100 is attached to the gas sensor 1, the lengths of the arm portions 120, 125, 130 and 135 in their extension directions are determined so that the leading ends 121, 126, 131 and 136 thereof may be arranged radially outside the outer periphery of the opening 32 of the outer cylinder 3 (refer to FIG. 5).

Further, the leading ends 121, 126, 131 and 136 of the respective arm portions 120, 125, 130 and 135 in their extension directions are connected together in the peripheral direction by an annular connecting portion 140. Also, a peripheral edge of the connecting portion 140 on its outer peripheral side extends toward the bottom surface side of the ventilation portion 110 in its thickness direction, and is formed as a latch portion 150 that forms a cylindrical shape. The internal diameter of the latch portion 150 is set to be slightly larger than the external diameter of the rear end of the outer cylinder 3, and the length of the latch portion in its extension direction (the thickness direction of the ventilation portion 110) is set such that it extends toward the leading end side further than the crimping portion 35 from the rear end of the outer cylinder 3. Further, a cutout that is closed on the side of an edge end 151 on the opening side (leading end side in the extension direction) of the latch portion 150 and that extends toward an edge end 152 on the side of the connecting portion 140 is provided in a peripheral wall of the latch portion 150, and an inwardly protruding portion 155 that protrudes toward the inner peripheral side of the latch portion 150 is formed by pushing a free end 156 on the opening side (edge end 152) of the cutout inward. Such inwardly protruding portions 155 are provided in six places that are spaced at almost regular intervals in the peripheral direction of the latch portion 150 (a configuration in which six inward protruding portions are provided is merely an example, and it is sufficient if one or more inwardly protruding portions are provided). Further, protruding portions 158 that are formed by pushing in the peripheral wall and making it protrude inward is provided in a position near the edge end 151 of the latch portion 150. The protruding portions 158 do not overlap the inwardly protruding portions 155, and are provided in three places that are spaced at almost regular intervals in the peripheral direction (two of them are shown in FIG. 3). In addition, although a configuration in which thrice protruding portions 158 are provided as an example, the protruding portions 158 are preferably provided in three or more places from the viewpoint of suppressing wobbling when the protective member 100 is attached to the outer cylinder 3.

The protective member 100 of such a configuration, as shown in FIGS. 4 and 5, is attached to the gas sensor 1 by putting the cylindrical latch portion 150 on the rear end of the outer cylinder 3 from the edge end 151 side, and arranging the ventilation portion 110 in a region where the inner periphery of the air vent 91 extends in the direction of the axis O on the rear end side of the filter member 87, and closing the air vent 91. At this time, the arm portions 120, 125, 130 and 135 of the protective member 100 are respectively arranged in the grooves 93, 94, 95 and 96 of the grommet 9, and the respective leading ends 121, 126, 131 and 136 are arranged outside the outer periphery of the opening 32 of the outer cylinder 3 so as to protrude outward through the grooves 93 and 95. Also, the latch portion 150 extending from the peripheral edge on the outer peripheral side of the connecting portion 140 that connects the respective leading ends 121, 126, 131 and 136 together is arranged so as to surround the outer peripheral surface on the rear end side of the outer cylinder 3. The protruding portion 158 of the latch portion 150 abuts the outer peripheral surface of a portion where the crimping portion 35 is not formed, in the outer peripheral surface of the outer cylinder 3, and the edge end 151 on the opening side of the latch portion 150 is positioned in the radial direction with respect to the outer cylinder 3 by the protruding portion 158. Further, the free end 156 of each of the inwardly protruding portions 155 that form an inward indented shape in the latch portion 150 abuts a wall surface (surface that faces the leading end) in a grooved recess that is formed by the crimping portion 35 on the rear end side of the outer cylinder 3.

Here, the angle of inclination of the grooves 93 to 96 in the direction of the axis O, and the angle of inclination of the arm portions 120, 125, 130 and 135 with respect to the ventilation portion 110 are set to be approximately equal to each other. For this reason, in a state where the inwardly protruding portions 155 of the latch portion 150 have been locked to the crimping portion 35, the grooves 93 to 96 and the arm portions 120, 125, 130 and 135 are brought into close contact with one another, respectively. As such, the protective member 100 is mechanically joined to the outer cylinder 3 by fitting (externally fitting) the inwardly protruding portions 155 into the rear end side of the outer cylinder 3 from the outside so as to lock the latch portion 150 to the crimping portion 35, and holding down the grommet 9 with the arm portions 120, 125, 130 and 135. In other words, the protective member 100 is mechanically joined to the outer cylinder 3 such that the grommet 9 that is made integral with the outer cylinder 3 is sandwiched between the arm portions 120, 125, 130 and 135 arranged in the grooves 93 to 96 of the grommet 9, and the inwardly protruding portions 155 of the latch portion 150 that abut the crimping portion 35.

In addition, as described above, even if the arm portions 120, 125, 130 and 135 of the first protective member 100 are not brought into close contact with the grooves 93 to 96, the connecting portion 140 abuts the rear end of the outer cylinder 3. Also, even if the outer cylinder 3 is sandwiched between the connecting portion 140 and the inwardly protruding portions 155 of the latch portion 150 that abut the crimping portion 35, the outer cylinder 3 can be mechanically joined to the protective member 100.

Further, as mentioned above, the crimping portion 35 of the outer cylinder 3 forms an annular groove that is depressed in the radial direction on the outer peripheral surface of the outer cylinder 3. The locking of the inwardly protruding portions 155 of the latch portion 150 to the crimping portion 35 is made as the free end 156 located on the rear end side of the inwardly protruding portion 155 in the direction of the axis O abuts the wall surface (surface that faces the leading end) on the rear end side of the crimping portion 35. Accordingly, the latch portion 150 will not be locked in the peripheral direction of the crimping portion 35. However, the arm portions 120, 125, 130 and 135 of the protective member 100 are respectively arranged in the grooves 93 to 96 of the grommet 9. Therefore, the inner walls of the grooves 93 to 96 act as stoppers, and limit rotation of the protective member 100 in the peripheral direction around the direction of the axis O. For this reason, the lead wires 18 inserted through the lead wire insertion holes 92 that are provided so as to avoid the grooves 93 to 96 of the grommet 9 do not contact the arm portions 120, 125, 130 and 135 of the protective member 100 positioned in the grooves 93 to 96. Further, since the lead wires 18 are arranged 1 mm or more away from any one of the arm portions 120, 125, 130 and 135 and the ventilation portion 110, even if the lead wires 18 are bent, any damage caused by contact therewith can be prevented.

Further, since the inwardly protruding portions 155 of the protective member 100 are formed by pushing the peripheral wall of the latch portion 150 inward, and have a spring property, their engagement can be maintained with a biasing force to the crimping portion 35 of the outer casing 3. Moreover, since positioning of the latch portion 150 in the radial direction is made by the protruding portions 158, the protective member 100 can make positive mechanical joining, without wobbling on the rear end side of the outer casing 3.

Also, because the wobbling of the protective member 100 is suppressed, wobbling of the ventilation portion 110 (arranged in a region where the inner periphery of the atmosphere communication hole 91 extends in the direction of the axis O on the rear end side of the filter member 87 which, in turn, is arranged in the air vent 91) is also suppressed with respect to the air vent 91. Accordingly, even if the ventilation portion 110 is subject to external impact, such as by contact with plants and trees, or by collision with scattering stones, protection of the filter member 87 from these impacts can be maintained, and damage to the filter member 87 can be reliably prevented. On the other hand, although the air vent 91 is closed by the ventilation portion 110, the air permeability in the air vent 91 via the ventilation portion 110 is secured by the openings 116 provided in the louver 115 of the ventilation portion 110. Also, because the entrance of water drops or the like into the outer cylinder 3 is prevented and the atmosphere is introduced, via the filter member 87, the reference electrode 62 of the detecting element 6 is exposed to the atmosphere, the detecting element 6 is operational, and the presence/absence of oxygen is detected.

Figure 6:
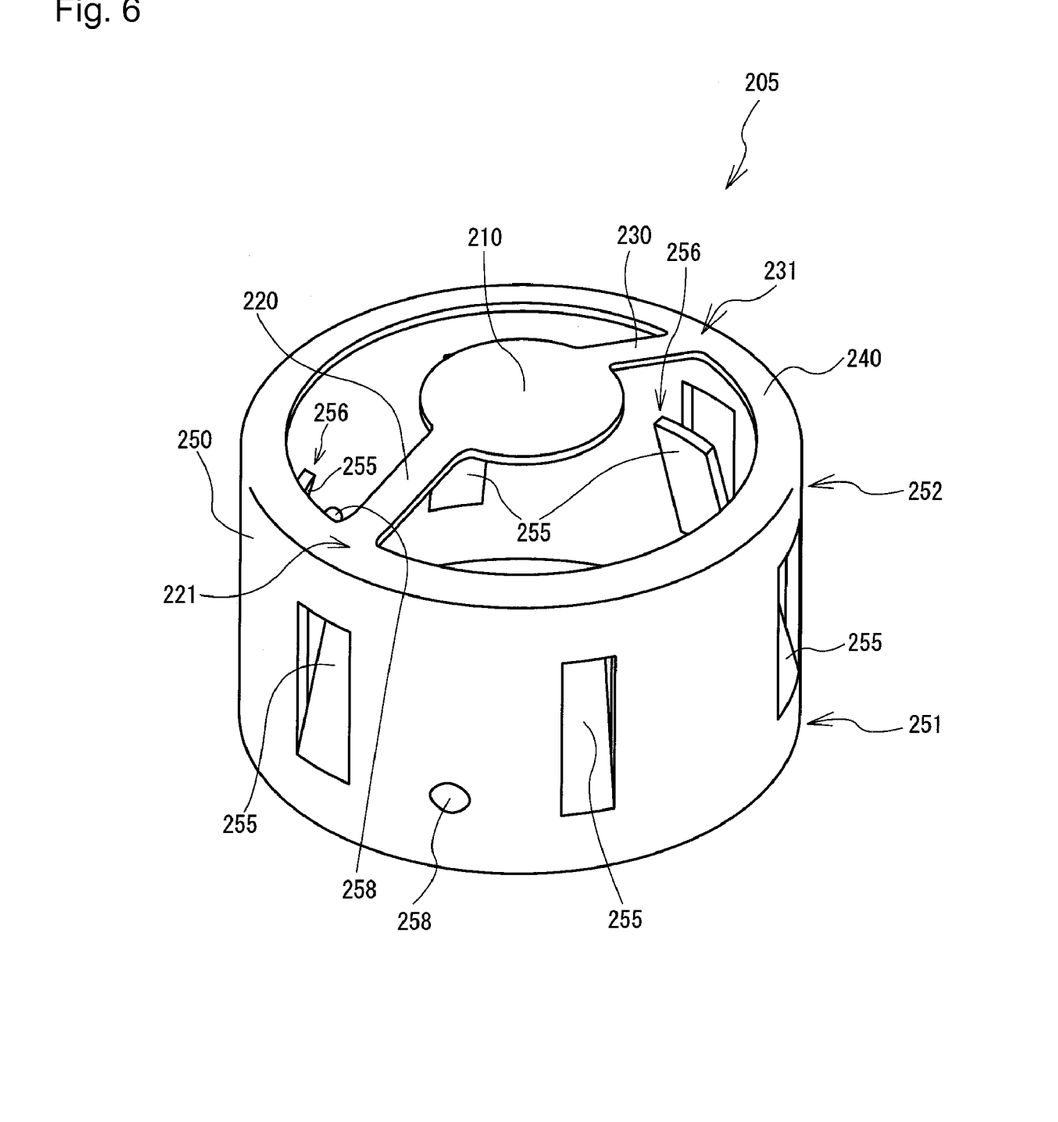
FIG. 6 is a perspective view of a protective member 205 of a second embodiment.
Figure 7:
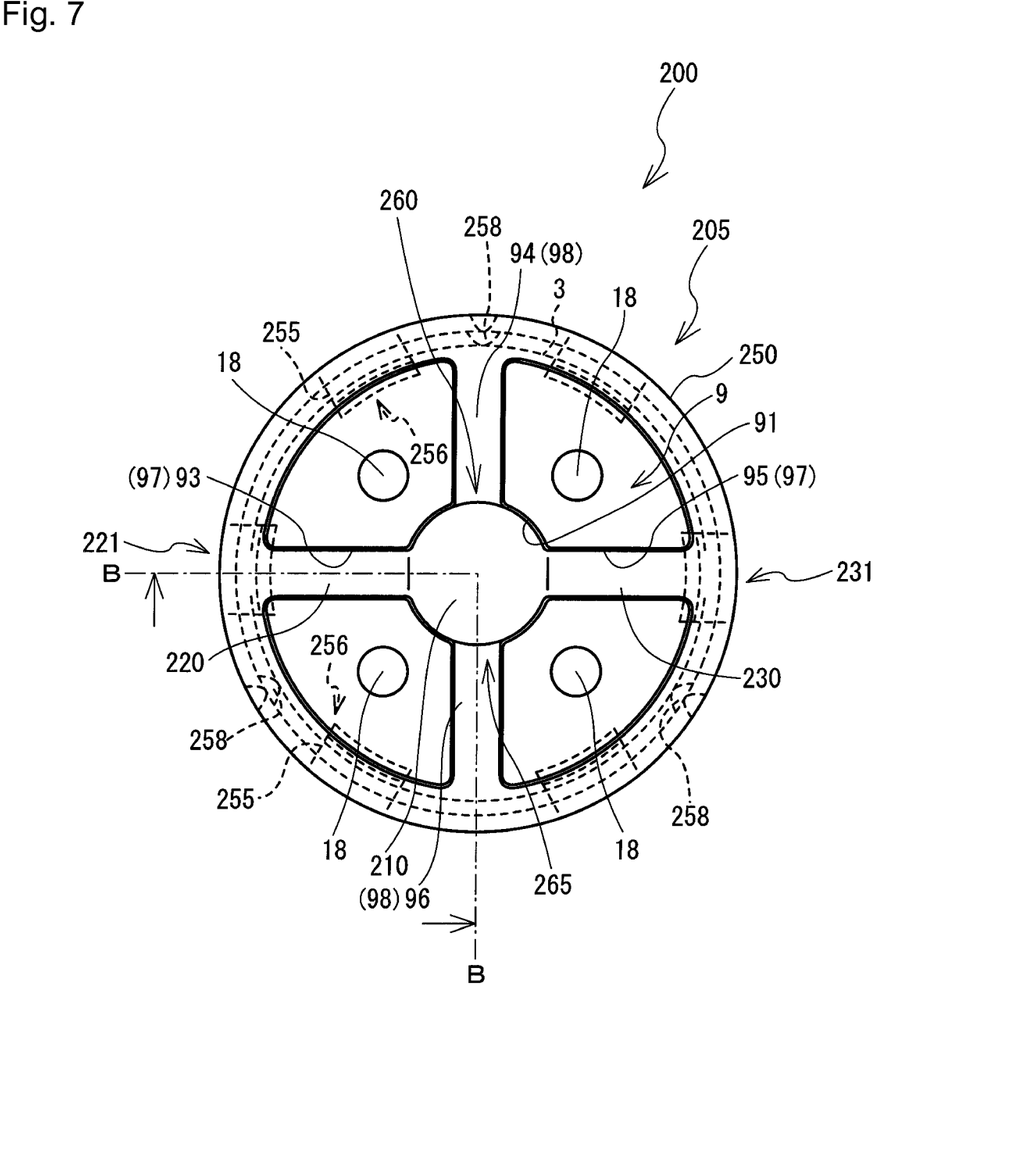
FIG. 7 is a view of a gas sensor 200 of the second embodiment when seen from the rear end side in the direction of an axis O (the upper side in FIG. 1).
Figure 8:
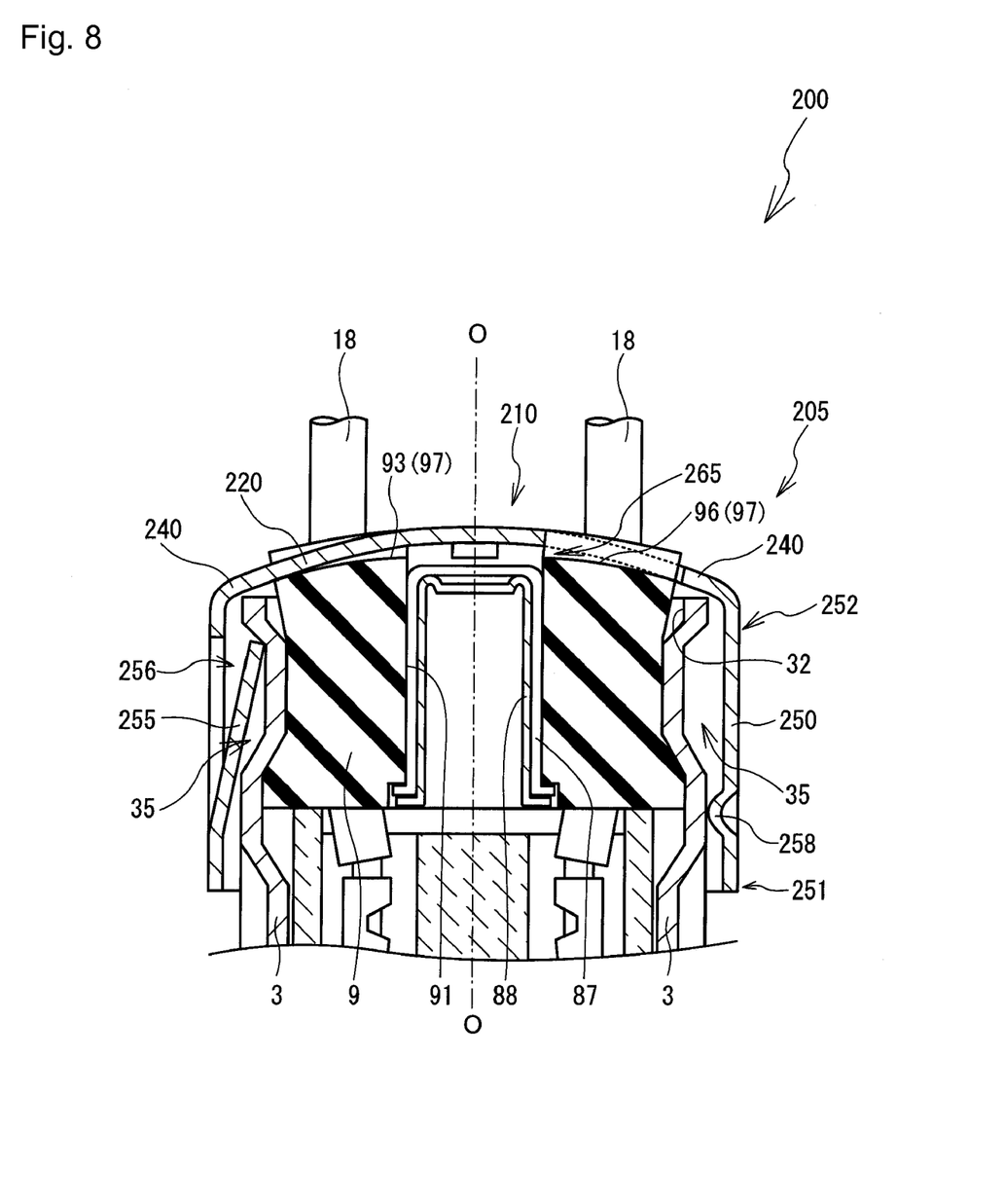
FIG. 8 is a partially enlarged sectional view of the rear end side of the gas sensor 200 of the second embodiment when seen from the direction of an arrow in a bent line B-B shown by a one-dot chain line of FIG. 7.

Next, as a second embodiment of the gas sensor according to the invention, a gas sensor 200 will be explained as an example referring to FIGS. 6 to 8. FIG. 6 is a perspective view of a protective member 205 of the second embodiment. FIG. 7 is a view when the gas sensor 200 of the second embodiment is seen from the rear end side in the direction of the axis O (the upper side in FIG. 1). FIG. 8 is a partially enlarged sectional view of the rear end side of the gas sensor 200 of the second embodiment when seen from the direction of an arrow in a bent line B-B shown by a one-dot chain line of FIG. 7.

The gas sensor 200 of the second embodiment is manufactured using the protective member 205 that has a different form from that of the protective member 100 used for the gas sensor 1 of the first embodiment. That is, the same parts as those of gas sensor 1 are used other than protective member 205 among parts constituting the gas sensor 200. Accordingly, the protective member 205 will be explained herein, and the description of other parts is omitted or simplified.

The protective member 205 shown in FIG. 6 is different from the protective member 100 of the first embodiment shown in FIG. 3, and is provided with a circular plate-like covering portion 210 instead of the ventilation portion 110. The covering portion 210 is not provided with an opening, and the size of the plate surface of the covering portion 210 is configured so as to be almost the same as the size of the opening of the air vent 91 (refer to FIG. 8). Two plate-like arm portions 220 and 230 that extend in two directions radially outward are formed at a peripheral edge of the covering portion 210. Leading ends 221 and 231 of the respective arm portions 220 and 230 in their extension directions are inclined toward the bottom surface side (downward) of the covering portion 210 in its thickness direction, and are connected in the peripheral direction by an annular connecting portion 240. Here, in the second embodiment, the angle of inclination of the arm portions 220 and 230 with respect to the covering portion 210 of the protective member 205 is set to be larger than the angle of inclination of the arm portions 120, 125, 130 and 135 with respect to the ventilation portion 110 of the protective member 100. In addition, the protective member 205 corresponds to the "second protective member" of the invention.

Also, a peripheral edge of the connecting portion 240 on its outer peripheral side extends toward the bottom surface side of the covering portion 210 in its thickness direction, and is formed as a latch portion 250 having a cylindrical shape. The configuration of the latch portion 250 is the same as that of the first embodiment, and a peripheral wall of the latch portion is formed with inward protruding portions 255 that are formed by pushing an end 256 on the opening side (on the side of an edge end 252) of a cutout inward, and protruding portions 258 that protrude inward in positions near the edge end 251.

The protective member 205 configured in this manner is attached to the gas sensor 200 by extension fitting the latch portion 250 to the rear end side of the outer casing 3, and locking the crimping portion 35 to the inwardly protruding portion 255, to thereby achieve mechanical joining in a manner similar to the first embodiment. At this time, the covering portion 210 having almost the same size as the opening of the air vent 91 is arranged so as to function as a lid of the air vent 91. For this reason, as shown in FIG. 7, when the gas sensor 200 is seen in the direction of the axis O (refer to FIG. 8) from the rear side, the filter member 87 covered with the covering portion 210 is largely hidden from view. This protects the filter member 87 from contact with plants and trees, or collisions with scattering stones, and prevents the filter member 87 from being damaged by external impact.

Further, since the angle of inclination of the arm portions 220 and 230 with respect to the covering portion 210 is different from that of the protective member 100 (refer to FIG. 3), as shown in FIG. 8, there is a resulting difference between the angle of inclination of the grooves 93 to 96 in the direction of the axis O of the grommet 9 and the angle of inclination of the arm portions 220 and 230 with respect to the covering portion 210. Of these, the arm portion 220 and associated grooves 93 and 96 are shown in FIG. 8. For this reason, the arm portions 220 and 230 of the protective member 205 form a gap between the grooves 93 and 95 on the side closer to the covering portion 210, although they abut the grooves 93 and 95 of the grommet 9. For this reason, the covering portion 210 is arranged so as to be supported by the arm portions 220 and 230 in positions that slightly deviate toward the rear end side in the direction of the axis O further than the positions of the bottoms of the grooves 93 to 96 on the side of the atmosphere communication hole 91. As a result, on the side of the grooves 94 and 96 (refer to FIG. 7) where an arm portion is not provided, gaps 260 and 265 (of these, the gap 265 is shown in FIG. 8) are produced between the covering portion 210 and the grommet 9. This secures air permeability between the inside and outside of the outer cylinder 3 via the atmosphere communication hole 91 through the gaps 260 and 265 in a state where the filter member 87 is not directly exposed to the outside via the air vent 91.

The invention is not limited to the above embodiment, and various changes can be made thereto. The ventilation portion 110 of the protective member 100 of the first embodiment is acceptable if it can prevent damage to the filter member 87 caused by external impact, such as by contact with plants and trees, or collision with scattering stones. For example, the plate surface of the ventilation portion 110 excluding its peripheral edge may be provided with an opening, and the opening may be provided with a metallic mesh member. Further, the mesh member need not be provided if the opening has a size such that external impact, such as by contact with plants and trees, or collision with scattering stones, can be prevented, and where air permeability may be secured by increasing the number of openings in the shape of pinholes, and by increasing the total opening area.

Further, two arm portions 220 and 230 are provided in the protective member 205 of the second embodiment in order to secure air permeability. However, three arm portions may be provided, or gaps for ventilation may be formed by providing four arm portions similarly to the protective member 100, and by making the width thereof smaller than the width of the grooves 93 to 96 of the grommet 9. Air permeability may also be secured by working the grommet 9 side, providing a cutout that communicates with the gaps between the arm portions 220 and 230 and the grooves 93 and 95 of the protective member 205, and introducing the atmosphere between the covering portion 210 and the filter member 87 via the cutout.

Further, although the inwardly protruding portion 155 is formed by making a slit in the outer peripheral surface of the protective member 100 and pushing its free end side inward, the slit may have an arbitrary shape. If the inwardly protruding portions 155 of such a form are provided, the inwardly protruding portions 155 can have a spring property, and can more reliably suppress wobbling of the protective member 100 with respect to the outer cylinder 3 while maintaining engagement with the crimping portion 35 with a biasing force. Of course, a projection may be joined to the inner peripheral surface of the latch portion 150, and the outer peripheral surface of the latch portion may be formed in the shape of a dowel that is pushed inward.

Figure 9:
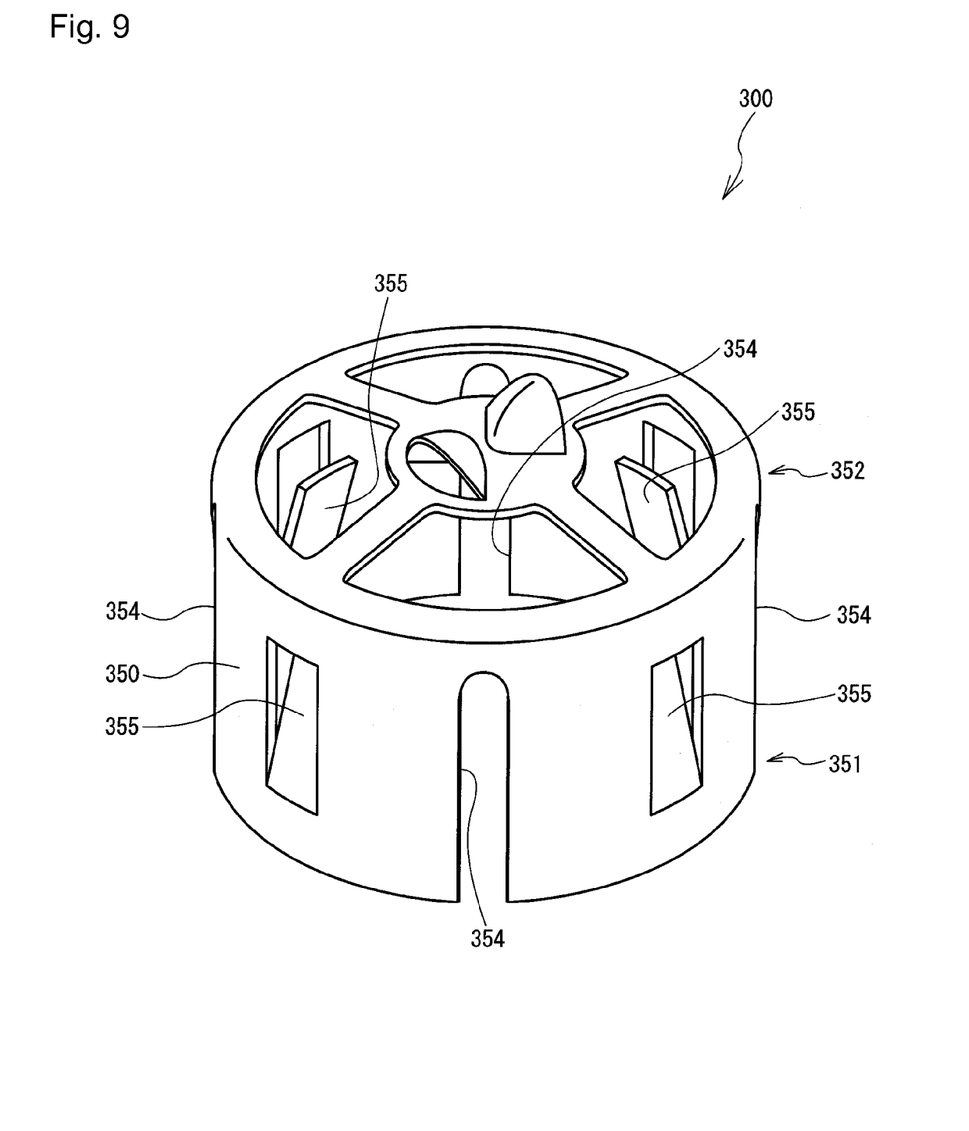
FIG. 9 is a perspective view of a modified example of protective member 300.

Further, in the protective member 300 shown in FIG. 9, a plurality of (for example, four) slit-like cut portions 354 are provided that extend toward an edge end 352 from an edge end 351 of a cylindrical latch portion 350. In this case, the cut portions 354 may be provided so as to be arranged alternately with the inwardly protruding portions 355 in the peripheral direction. If the inwardly protruding portions 355 that are pushed inward abut the outer peripheral surface of the outer cylinder 3 when the protective member 300 is attached to the gas sensor, a stress that pushes and bends the inwardly protruding portions 355 is applied. Therefore, it becomes difficult to fit the latch portion 350 to the rear end side of the outer cylinder 3. However, by providing the cut portions 354 in this manner, the edge end 351 of the latch portion 350 can be slightly bent with the edge end 352 as a support. Thus, fitting of the latch portion 350 to the rear end side of the outer cylinder 3 can be performed easily. Further, although not shown, the same protruding portions 158 as those of the protective member 100 are preferably provided in the latch portion 350 to suppress wobbling of the latch portion 350 with respect to the outer cylinder 3.

Further, the grooves 93 to 96 need not be formed in the grommet 9. In this case, at least a pair of protruding portions may be provided on the ceiling surface 99 of the grommet 9, and the arm portions 120, 125, 130 and 135 of the protective member 100 may be arranged in positions that are sandwiched by the protruding portions. Otherwise, the grooves 93 to 96 may be formed partially in the shape of a groove. That is, grooves may be formed in the vicinity of the air vent 91, but may be reduced in depth toward the outer peripheral or their depth may disappear, and may be made flush with the ceiling surface 99. Further, the number of grooves one may be one or may be two or more, and the number is not limited to four.

Further, a concave portion or a pair of convex portions may be provided in the opening 32 of the outer casing 3, and the protective member 100 may be assembled so that the arm portions 120, 125, 130 and 135 are arranged in the convex portion or between the pair of convex portions, thereby limiting rotation of the protective member 100 in a peripheral direction around the axis. Further, when crimping is performed in the vicinity of the opening 32 of the outer casing 3 to form the crimping portion 35, even if a convex portion that limits rotation of the latch portion 150 in the peripheral direction is provided in the crimping portion 35, and even if partial crimping is performed in the peripheral direction, the rotation of the protective member 100 in a peripheral direction around the axis can similarly be regulated.

It should further be apparent to those skilled in the art that various changes in form and detail of the invention as shown and described above may be made. It is intended that such changes be included within the spirit and scope of the claims appended hereto.

This application is based on Japanese Patent Application JP 2007-113100, filed Apr. 23, 2007, the entire content of which is hereby incorporated by reference, the same as if set forth at length.

What is claimed is:

1. A gas sensor having an axis comprising:
  a detecting element extending in an axial direction of the gas sensor, and having a detecting portion for detecting a gas to be detected on a leading end side of the detecting element;
  a metal shell surrounding a radial periphery of the detecting element such that the detecting portion protrudes from a leading end of the metal shell;
  an outer cylinder that is fixed to the metal shell, and which surrounds the radial periphery of a rear end portion of the detecting element; and
  a plug member provided in a rear end of the outer cylinder, the plug member including a lead wire insertion hole through which a lead wire is inserted, and an air vent provided with a filter member having air permeability and waterproofness,
  wherein the gas sensor comprises a first protective member that covers the air vent of the plug member so as to protect the filter member, the first protective member having a ventilation portion having an opening smaller than an opening of the air vent and at least partially overlapping the air vent in the axial direction, and
  at least one of the outer cylinder and the plug member is provided with a locking portion that limits rotation of the first protective member around the axis.

2. The gas sensor according to claim 1, wherein the first protective member is mechanically joined to the outer cylinder so that the first protective member is spaced away from the lead wire.

3. The gas sensor according to claim 1, wherein the distance between the first protective member and the lead wire is 1 mm or more.

4. The gas sensor according to claim 1, wherein the first protective member comprises a plurality of arm portions that extend radially outward from the ventilation portion and a cylindrical latch portion that is connected to individual ones of the plurality of the arm portions, said cylindrical latch portion surrounding the radial periphery of the rear end of the outer cylinder and being mechanically joined to the outer cylinder,
  the locking portion comprises a groove which extends radially outward from the air vent on a rear end surface of the plug member so as to avoid the lead wire insertion hole, and
  at least one of the arm portions is provided in the groove.

5. The gas sensor according to claim 4, wherein the latch portion that has a cylindrical shape comprises a plurality of inwardly protruding portions engaged with a crimping portion formed in an outer peripheral surface of the outer cylinder.

6. The gas sensor according to claim 4, wherein the groove is a connecting groove that symmetrically extends radially outward from the air vent on the rear end surface of the plug member, and two of the plurality of arm portions are provided in the connecting groove.

7. The gas sensor according to claim 1, wherein the ventilation portion of the first protective member comprises at least one of (i) a plurality of holes penetrating therethrough; and (ii) a mesh member assembled to an axial opening provided in the ventilation portion of the first protective member.

8. The gas sensor according to claim 1, wherein the first protective member has a hardness greater than that of the filter member.

9. A gas sensor having an axis comprising:
  a detecting element extending in an axial direction of the gas sensor, and having a detecting portion for detecting gas to be detected on a leading end side of the detecting element;
  a metal shell surrounding a radial periphery of the detecting element such that the detecting portion protrudes from a leading end of the metal shell;
  an outer cylinder that is fixed to the metal shell, and which surrounds the radial periphery on a rear end side of the detecting element; and
  a plug member provided in a rear end of the outer cylinder, the plug member including a lead wire insertion hole through which a lead wire is inserted, and an air vent provided with a filter member having air permeability and waterproofness,
  wherein the gas sensor comprises a second protective member that has a covering portion that covers the filter member so that the filter member cannot be viewed in the axial direction from the rear side, the second protective member being mechanically joined to the outer cylinder so as to form a gap between the second protective member and the plug member, and allowing ventilation between the inside and outside of the air vent, and at least one of the outer cylinder and the plug member is provided with a locking portion that limits rotation of the second protective member around the axis.

10. The gas sensor according to claim 9, wherein the second protective member is mechanically joined to the outer cylinder so that the second protective member is spaced away from the lead wire.

11. The gas sensor according to claim 9, wherein the distance between the second protective member and the lead wire is 1 mm or more.

12. The gas sensor according to claim 9, wherein the second protective member comprises a plurality of arm portions that extend radially outward from the covering portion and a cylindrical latch portion that is connected to individual ones of the plurality of the arm portions, said cylindrical latch portion surrounding the radial periphery of the rear end of the outer cylinder and being mechanically joined to the outer cylinder, the locking portion comprises a groove which extends radially outward from the air vent on a rear end surface of the plug member so as to avoid the lead wire insertion hole, and at least one of the arm portions is provided in the groove.

13. The gas sensor according to claim 12, wherein the latch portion that has a cylindrical shape comprises a plurality of inwardly protruding portions engaged with a crimping portion formed in an outer peripheral surface of the outer cylinder.

14. The gas sensor according to claim 12, wherein the groove is a connecting groove that symmetrically extends radially outward from the air vent on the rear end surface of the plug member, and two of the plurality of arm portions are provided in the connecting groove.

15. The gas sensor according to claim 9, wherein the second protective member has a hardness greater than that of the filter member.

* * * * *